United States Patent [19]

Lipinski

[11] Patent Number: 4,680,306

[45] Date of Patent: Jul. 14, 1987

[54] SPRIO-IMIDAZOLONES FOR TREATMENT OF DIABETES COMPLICATIONS

[75] Inventor: Christopher A. Lipinski, Waterford, Conn.

[73] Assignee: Pfizer Inc., New York, N.Y.

[21] Appl. No.: 842,109

[22] PCT Filed: Jul. 20, 1984

[86] PCT No.: PCT/US84/01155
§ 371 Date: Mar. 14, 1986
§ 102(e) Date: Mar. 14, 1986

[87] PCT Pub. No.: WO86/00807
PCT Pub. Date: Feb. 13, 1986

[51] Int. Cl.⁴ ............... A61K 31/415; C07D 491/107; C07D 495/10
[52] U.S. Cl. .................... 514/389; 548/309; 549/70; 549/72; 549/73; 549/483; 549/488
[58] Field of Search .................. 548/309; 514/389

[56] References Cited

U.S. PATENT DOCUMENTS

| | | | |
|---|---|---|---|
| 3,821,383 | 6/1974 | Sestanj et al. | 514/278 |
| 3,985,888 | 10/1976 | Carr et al. | 514/278 |
| 4,117,230 | 9/1978 | Sarges | 548/309 |
| 4,127,665 | 11/1978 | Sarges et al. | 548/309 X |
| 4,130,714 | 12/1978 | Sarges | 548/309 |
| 4,147,797 | 4/1979 | Kelbaugh et al. | 548/309 X |
| 4,248,882 | 2/1981 | Sarges et al. | 548/309 X |
| 4,386,100 | 5/1983 | Brittain et al. | 548/309 X |
| 4,503,066 | 3/1985 | Brittain et al. | 514/409 |
| 4,575,507 | 3/1986 | Lipinski | 548/309 X |

*Primary Examiner*—Richard A. Schwartz
*Attorney, Agent, or Firm*—Charles J. Knuth; Peter C. Richardson; Robert F. Sheyka

[57] ABSTRACT

Spiro-imidazolones are disclosed which are useful as aldose reductase inhibitors and as therapeutic agents for the treatment of complications arising from diabetes. Pharmaceutical compositions containing the spiro compounds and a method of treating diabetic complications are also disclosed.

8 Claims, No Drawings

SPIRO-IMIDAZOLONES FOR TREATMENT OF DIABETES COMPLICATIONS

TECHNICAL FIELD

This invention relates to novel spiro-imidazolones useful in the treatment of certain chronic complications arising from diabetes mellitus, such as diabetic cataracts, retinopathy and neuropathy, to pharmaceutical compositions containing such compounds and to a method of using these compounds

BACKGROUND ART

In the past various attempts have been made to obtain more effective oral anti-diabetic agents. Generally these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1, 3-dioxo-1H-benz[d,e]-isoquinoline-2(3H)-acetic acid and derivatives thereof to be useful for the treatment of these conditions. U.S. Pat. No. 4,117,230 teaches the use of certain hydantoins for treating complications of diabetes as aldose reductase inhibitors. Such aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way unwanted accumulations of galactitol in the lens of galactosemic subjects and of sorbitol in the lens, of peripheral nervous cord and kidneys of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

Carr et al., U.S. Pat. No. 3,985,888, teach certain spiroalkanone-imides and their use as sedatives. European Patent Application Publication No. 0065392 discloses certain spiro-succinimide derivatives and their use as aldose reductase inhibitors.

Sarges et al. in U.S. Pat. No. 4,127,665 disclose that certain thiophene spiro-imidazolidindiones are useful as aldose reductase inhibitors.

DISCLOSURE OF INVENTION

The compounds of the present invention are spiroimidazolones of the formula

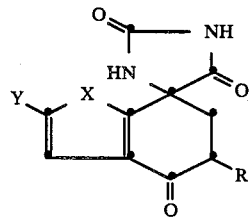

or a pharmaceutically acceptable salt thereof, wherein X is oxygen or sulfur, Y is hydrogen, halo or alkyl having 1-4 carbon atoms, and R is hydrogen, methyl or ethyl.

Preferred compound are those wherein R is hydrogen or methyl, Y is hydrogen and X is sulfur.

Both mixtures of optically active isomers and partially or completely optically resolved isomers of the compounds claimed herein are within the scope of the present invention.

Also embraced by the present invention are pharmaceutical compositions comprising a pharmaceutically acceptable carrier or diluent and a compound of formula I. The present invention further comprises a method of treating a diabetic host for diabetes-associated complications which comprises administering to the host an effective amount of a compound of formula I.

DETAILED DESCRIPTION

The numbering system of the spiro compounds of formula I is as shown.

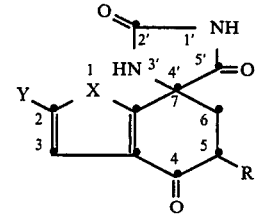

The compounds are spiro[benzo[b]-thiophene (X=S) or furan (X=O) -7(6H), 4'-imidazolidine]-2',5'-dione-2-Y-5-R-4-ones.

Compounds of formula I can be prepared according to the Synthetic Scheme described hereinafter.

The aldehyde of formula II is reacted with 1-methyl- or 1-ethyl-cyanoethylene if R is methyl or ethyl, respectively, in the presence of an alkali metal cyanide such as sodium or potassium cyanide, preferably sodium cyanide in an aprotic polar organic solvent such as dimethylformamide at a temperature range of about 0 to 60° C., preferably about 35° C., to obtain the condensation product of formula III. The compounds of formula III wherein Y is hydrogen and R is hydrogen are known.

The cyano group of formula III is hydrolyzed in a strong aqueous mineral acid at about 60° C. to the solvent reflux temperature, for example, hydrochloric acid in refluxing formic acid, to obtain the corresponding carboxylic acid of formula IV.

Alternatively the compounds of formula IV can be prepared by condensing a compound of formula II with an acrylate, methacrylate or ethacrylate alkyl ester wherein the alkyl has 1-7 carbon atoms, using the same conditions as used to prepare compounds of formula III. The resulting condensation products are hydrolyzed using an aqueous base such as sodium hydroxide or ammonium hydroxide at a pH of between about 9 and 12 at about 0 to 60° C., preferably about 25° C.; for example, 0.1N sodium hydroxide in aqueous tetrahydrofuran. This procedure may be employed with acid-sensitive compounds.

The compound of formula IV in an aqueous solution such as in water is heated at about 50 to 100° C., preferably about 70° C . with ammonium carbonate and an alkali metal cyanide such as potassium cyanide to obtain the imidazolidone of formula V.

The desired compound of formula I is obtained by acid catalyzed ring closure of a compound of formula V in a reaction inert solvent at about 0° C. to the solvent reflux temperature. An acid such as hot, concentrated sulfuric or polyphosphoric acid may be employed. When sulfuric acid is employed a temperature range of about 50 to 90° C., preferably about 70° C. may be used. Lewis acids such as aluminum trichloride or titanium tetrachloride in a reaction-inert solvent such as benzene or toluene can be used at temperture ranges between about 0° C. and the solvent reflux temperature, depending on the nature of the Y substituent.

SYNTHETIC SCHEME

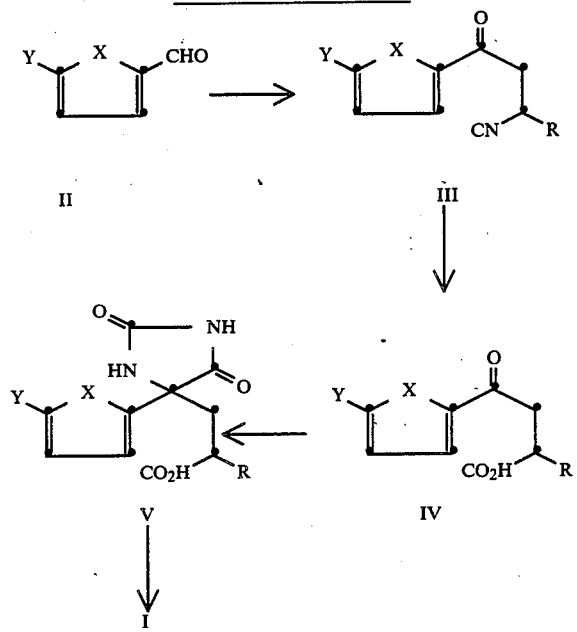

Diastereomers can be separated by methods known in the art such as recrystallization with a suitable solvent such isopropanol or trituration, for example, with an alcohol-ether solvent such as isopropanol-diethyl ether. The terms "Rel" and "(+)" each mean a 1:1 racemic mixture of the two optically active enantiomers.

Because of the acidic hydrogen atom in the spiro heterocyclic ring of the compounds of formula I, salts may be formed with pharmaceutically acceptable cations by conventional methods. Thus, these salts may be readily prepared by treating the compound of formula I with an aqueous solution of the desired pharmaceutically acceptable cation and evaporating the resulting solution to drynes, preferably under reduced pressure. Alternatively, a lower alkyl alcohol solution of the compound of formula I may be mixed with an alkoxide of the desired cation and subsequently evaporating the solution to dryness. Suitable pharmaceutically acceptable cations for this purpose include, but are not limited to, alkali metal cations such as potassium and sodium, ammonium or water soluble amine addition salts such as the lower alkanolammonium and other base salts with organic amines which are pharmaceutically acceptable and alkaline earth metal cations such as calcium and magnesium.

When Y is halo, halo can be fluoro, chloro, bromo or iodo.

Pharmaceutically acceptable salts are those which do not cause unacceptable adverse reactions when administered.

The novel compounds of formula I and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention and alleviation of such conditions. The compound may be administered to a mammalian subject in need of treatment by a variety of conventional routes of administration, including orally, parenterally and topically. In general, these compounds will be administered orally or parenterally at dosages between about 0.05 and 25 mg./kg. body weight of the subject to be treated per day, preferably from about 0.1 to 10 mg./kg. per day. However, some variation in dosage will necessarily occur depending on the condition of the subject being treated. The person responsible for administration will, in any event, determine the appropriate dose for the individual subject.

The novel compound of the invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral adminstration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal adminsitration. In this connection, the sterile aqueous media employed are all readily available by standard techniques known to those skilled in the art.

Compounds of formula I may not only be advantageously employed for the preparation of aqueous pharmaceutical compositions for parenteral administration, as described above, but more particularly for the preparation of pharmaceutical compositions suitable for use as ophthalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts the compounds of this invention are administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.). The ophthalmic preparation will contain a compound of formula I, or a pharmaceutically acceptable salt thereof, in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potasssium borate, sodium and potassium carbonate, sodium acetate, sodium biphosphate and the like, in amounts sufficient to maintain the pH at between about 6 and 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve and lens of acutely streptozotocinized, i.e. diabetic, rats; (3) measuring their ability to reverse already-elevated sorbitol levels in the sciatic nerve and lens of chronic streptozotocin-induced diabetic rats; (4) measuring their ability to prevent or inhibit galacticol formation in the lens of acutely galactosemic rats; (5) measuring their ability to delay cataract formation and reduce the severity of lens opacities in chronic galactosemic rats; (6) measuring their ability to prevent sorbitol accumulation and cataract formation in isolated rat lens incubated with glucose; and (7) measuring their ability to reduce already elevated sorbitol levels in isolated rat lens incubated with glucose.

The present invention is illustrated by the following examples. It will be understood, however, that the invention is not limited to the specific details of these examples. Proton nuclear magnetic resonance spectra (NMR) were measured at 250 MHz (unless otherwise indicated) for solutions in perdeuterodimethyl sulfoxide (DMSO-$d_6$) and peak positions are expressed in parts per million (ppm) downfield from tetramethylsilane. The peak shapes are denoted as follows: s, singlet; d, doublet; t, triplet; q, quartet; m, multiplet; b, broad; very, v.

EXAMPLE 1

Spiro[benzo[b]thiophene-7(6H),4'-imidazolidine]-2',5'-dione-5H-4-one 1.3 g (5.1 mmol) 4-Imidazolidinepropionic acid 4-(2-thienyl) 2, 5-dioxo was combined with 13 ml of concentrated sulfuric acid and stirred at 70° C. for 4 hours. The reaction was cooled and quenched with ice. The resultant grey-brown solid which formed was collected by filtration, washed with water and partially dried in vacuo. This solid material was partitioned between ethyl acetate and water and the aqueous layer was washed with ethyl acetate. The combined ethyl acetate layers were backwashed with water and then slurried with activated charcoal admixed with diatomaceous earth filter aid and then filtered to give a clear ethyl acetate solution. This solution was concentrated in vacuo to a white foam. A white solid formed from the foam upon trituration with diethyl ether and was collected by filtration, washed with diethyl ether and dried at 110° C. in vacuo to give 100 mg of spiro [benzo[b]thiophene-7(6H),4'-imidazolidine]-2', 5'-dione-5H -4-one . NMR (DMSO-$d_6$) : 11.2 (vb s, 1H,) 8.89 (s, 1H,) 7.65 (d, 1H), 7.35 (d, 1H), 2.85–3.05 (m, 1H), a (m, 3H) ppm. Anal. Calc'd. for $C_{10}H_8N_2O_3S$: C, 50.84; H, 3.41; N, 11.86. Found: C, 51.14; H, 3.76; N, 11.23.

EXAMPLE 2

Spiro[benzo[b]thiophene-7(6H), 4'-imidazolidine]2', 5'-dione-5-methyl-4-one 1.36 g (5.0 mmol) 4-Imidazolidinepropionic acid alpha-methyl 4-(2-thienyl) 2,5-dioxo was combined with 14 ml of concentrated sulfuric acid and heated at 70° C. for 4 hours. The reaction mixture was cooled to 250° C., quenched with ice and the resultant grey-brown solid was collected by filtration, washed with water and air dried. The crude solid was partitioned between water and ethyl acetate. The aqueous layer was washed with ethyl acetate and the combined ethyl acetate layers were backwashed with water and then slurried with activated charcoal admixed with diatomaceous earth filter aid and filtered. The clear ethyl acetate solution filtrate was concentrated in vacuo to a white solid. Trituration with diethyl ether gave a white solid which was collected by filtration, washed with diethyl ether and dried at 110° C. in vacuo for 20 hours to give 0.40 g spiro[benzo[b]-thiophene -7(6H), 4'-imidazolidine]2',5'-dione-5-methyl-4-one: mp 226–228° C. with decomposition. NMR (DMSO-$d_6$) indicated the presence of two diastereomers in the ratio 87:13. NMR(DMSO-$d_6$): 11.15 (vb s, 1H), 9.04 (s, 0.13×1H), 8.85 (s, 0.87×1H), 7.68 (d, 0.13×1H), 0.87×1H), 7.35 (d, 0.87×1H), 7.32 (d, 0.13×1H), (m, 0.87×1H), 3.0 (m, 0.13×1H), 2.15-2.65 (m, 2H), 1.17 (d, 0.13×1H), and 1.15 (d, 0.87×1H) ppm. Anal. Calcd for $C_{11}H_{10}N_2O_3S$: C, 52.79; H, 4.03; N, 11.19. Found: C, 52.67, H, 4.19; N, 10.79.

PREPARATION A

4-Imidazolidinepropionic acid 4-(2-thienyl)-2,5-dioxo 2.3 g (12.5 mmol) 2-Thienylbutanoic acid-gamma-oxo was combined with 6.0 g (62.5 mmol) ammonium carbonate and 1.63 g (25 mmol) potassium cyanide in 30 ml water and stirred at 70° C. for 24 hours. The reaction was cooled to 25° C. and was acidified by dropwise addition of 10 ml of concentrated hydrochloric acid. A tan solid formed and was collected by filtration, washed with water and dried at 60° C. in vacuo to give 1.4 g of 4-imidazolidine-propionic acid 4-(2-thienyl)-2,5-dioxo: mp 176°-178° C. NMR(DMSO-$d_6$): 10.56 (vb s, 1H), 8.45 (s, 1H), 7.46-77 (m, 1H), 6.93-7.33 (m, 2H), and 2.0-2.46 (m, 4H) ppm.

PREPARATION B

4-Imidazolidinepropionic acid alpha-methyl-4-(2-thienyl)2, 5-dioxo 2.3 g (11.6 mmol) 2-Thienylbutanoic acid alpha-methyl-gamma-oxo was combined with 5.77 g (60 mmol) ammonium carbonate and 1.56 g (24 mmol) potassium cyanide in 30 ml water and heated at 70° C. for 48 hours. An additional 1.15 g (12 mmol) ammonium carbonate was added and heating was continued for an additional 24 hours. The reaction was cooled to 0° C. and acidified with concentrated hydrochloric acid. A tan solid which formed was collected by filtration, washed with water and dried in a vacuum oven for 60 hours to give 1.48 g 4-imidazolidinepropionic acid alpha-methyl4-(2-thienyl)2, 5-dioxo: mp 205°-208° C. containing a small amount of starting material (shown by thin layer chromatography). NMR (DMSO-$d_6$) showed a mixture of two diastereomers in the ratio 83:17:11.33 (vb s, 1H), 9.13 (s, 0.83×1H), 8.53 (s, 0.17×1H), 7.87 (d, 0.17×1H), 7.40 (d, 0.83×1H), 6.82-7.1 (m, 2H), 1.83-2.60 (m, 3H), 0.93-1.33 (m, 3H) ppm.

PREPARATION C

2-Thienylbutanoic acid-gamma-oxo 4.88 g (29.5 mmol) 2-Thienylbutyronitrile -gamma-oxo was combined with 25 ml concentrated hydrochloric acid and 25 ml concentrated formic acid and heated at reflux for 2 hours. The reaction mixture was cooled to 25° C., made strongly basic (pH=13) with sodium hydroxide and washed with ethyl acetate. The resulting red aqueous base solution was cooled and acidified to pH 2 with concentrated hydrochloric acid and the resultant reddish solid was collected by filtration and dried in vacuo at 40° C. to give 2.47 g of 2-thienylbutanoic acid -gamma-oxo: mp 106°-108° C. with decomposition. NMR (DMSO-$d_6$): 7.96 (d, 2H), 7.13 (t, 1H), 3.0-3.33 (m, 2H), 2.37-2.73 (m, 2H)ppm.

PREPARATION D

2-Thienylbutanoic acid alpha-methyl-gamma-oxo 6.75 g (37.7 mmol) 2-Thienylbutyronitrile alpha-methyl-gamma-oxo was combined with 25 ml concentrated hydrochloric acid and 25 ml neat formic acid and heated at reflux for 2 hours. The reaction mixture was cooled and made basic (pH=13) with sodium hydroxide. Most of the dark red color in the reaction was removed by washing with ethyl acetate. The aqueous layer was cooled to 0° C. and brought to pH 1 with concentrated hydrochloric acid. On standing a red solid formed which was collected by filtration and dried at 40° C. in vacuo overnight to give 2.39 g 2-thienylbutanoic acid alpha-methyl-gamma-oxo: mp 108°-110° C. with decomposition. NMR (DMSO-$d_6$) 7.98 (d, 2H ), 7.17 (t, 1H), 2.63-3.63 (m, 3H), and 1.13 (d, 3H) ppm.

PREPARATION E

2-Thienylbutyronitrile alpha-methyl-gamma-oxo 2.45 g (0.05 mol) Sodium cyanide was slurried in 50 ml dimethylformamide at 35° C. A solution of (1.2 g (0.10 mol) 2-thiophenecarboxaldehyde in 50 ml dimethylformamide was added dropwise over 20 min. After stirring at 35° C. for an additional forty minutes, 5.0 g (0.075 mol) methacrylonitrile in 20 ml dimethylformamide was added dropwise over 1.25 hours The reaction mixture was stirred an additional 3 hours and then was diluted with 75 ml methylene chloride and filtered to remove undissolved sodium cyanide. The methylene chloride layer was washed successively with 250 ml 0.22 N hydrochloric acid, two 100 ml portions water, 250 ml 0.22 N hydrochloric acid, 150 ml saturated aqueous sodium bicarbonate, 100 ml 1 N hydrochloric acid, two 75 ml portions water and finally 100 ml saturated aqueous sodium chloride solution. After drying over anhydrous sodium sulfate, the methylene chloride was combined with 100 ml methanol and decolorized with activated charcoal. Following filtration the solution was concentrated in vacuo to give 7.24 g of crude 2-thienylbutyronitrile alpha-methyl-gamma-oxo as a low melting solid containing some residual dimethylformamide. NMR (DMSO-$d_6$): 7.96 (d, 1H), 7.20 (t, 2H), 2.93-3.73 (m, 3H), and 1.33 (d, 2H) ppm.

We claim:
1. A compound of the formula

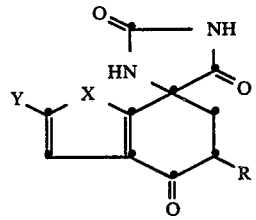

or a pharmaceutically acceptable salt thereof, wherein:
X is oxygen or sulfur;
Y is hydrogen, halo or alkyl having 1-4 carbon atoms; and
R is hydrogen, methyl or ethyl.
2. A compound according to claim 1 wherein X is sulfur.
3. A compound according to claim 2 wherein Y is hydrogen and R is hydrogen.
4. A compound according to claim 2 wherein Y is hydrogen and R is methyl.
5. A pharmaceutical composition comprising a compound according to claim 1 in an amount effective for the treatment of diabetes-associated complications and a pharmaceutically acceptable carrier or diluent.

6. A pharmaceutical composition according to claim 5 where X is sulfur, Y is hydrogen and R is hydrogen or methyl.

7. A method for treating diabetes complications in a mammal comprising administering an effective amount of a compound according to claim 1.

8. A method according to claim 7 wherein X is sulfur, Y is hydrogen and R is hydrogen or methyl.

* * * * *